United States Patent [19]
Scarfone et al.

[11] Patent Number: 5,669,883
[45] Date of Patent: Sep. 23, 1997

[54] VERESS NEEDLE AND CANNULA ASSEMBLY

[75] Inventors: Frank A. Scarfone, Miramar; Juan J. Arias, Hialeah, both of Fla.

[73] Assignee: Symbiosis Corporation, Miami, Fla.

[21] Appl. No.: 420,864

[22] Filed: Apr. 12, 1995

[51] Int. Cl.$^6$ .................................................. A61M 5/178
[52] U.S. Cl. ........................ 604/167; 604/158; 604/256
[58] Field of Search .......................... 604/26, 164, 158, 604/167, 256; 606/185

[56] References Cited

U.S. PATENT DOCUMENTS

| | | | |
|---|---|---|---|
| 4,430,081 | 2/1984 | Timmermans | 604/256 |
| 4,791,937 | 12/1988 | Wang | 604/164 |
| 4,869,717 | 9/1989 | Adair | 604/26 |
| 5,334,159 | 8/1994 | Turkel | 604/158 |
| 5,415,666 | 5/1995 | Gourlay et al. | 606/142 |

Primary Examiner—Robert A. Hafer
Assistant Examiner—Benjamin U. Koo
Attorney, Agent, or Firm—David P. Gordon

[57] ABSTRACT

A Veress needle and cannula assembly includes a stainless steel cannula assembly with a cannula having an outer diameter of approximately 4 mm and a Veress needle assembly having a Veress needle with an outer diameter of approximately 3 mm. The cannula assembly includes a proximal valve assembly and the Veress needle is insertable through the valve assembly. Where the cannula and Veress needle are not closely fitted, a molded transition collar on the Veress needle seals the annular space between the interior of the cannula and the exterior of the Veress needle and is provided with sharp distal edges for aiding insertion of the cannula assembly into the body of a patient. The cannula valve assembly preferably includes a female luer lock connector. The Veress needle preferably includes a handle with a rotatable male luer lock coupler which engages the female luer lock connector on the cannula valve assembly when the Veress needle is inserted into the cannula assembly.

13 Claims, 4 Drawing Sheets

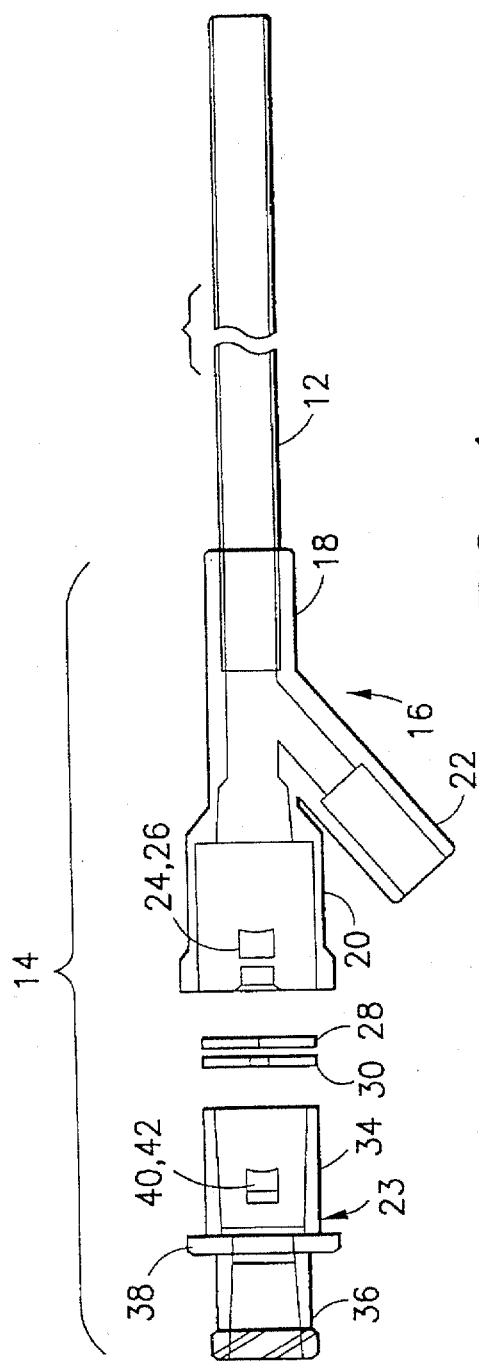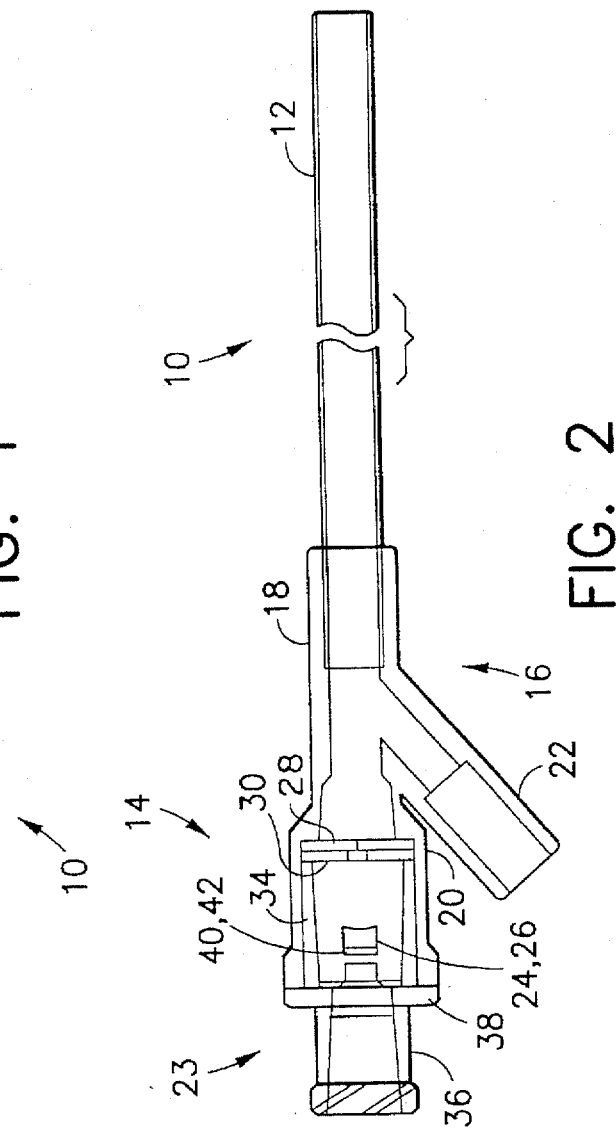

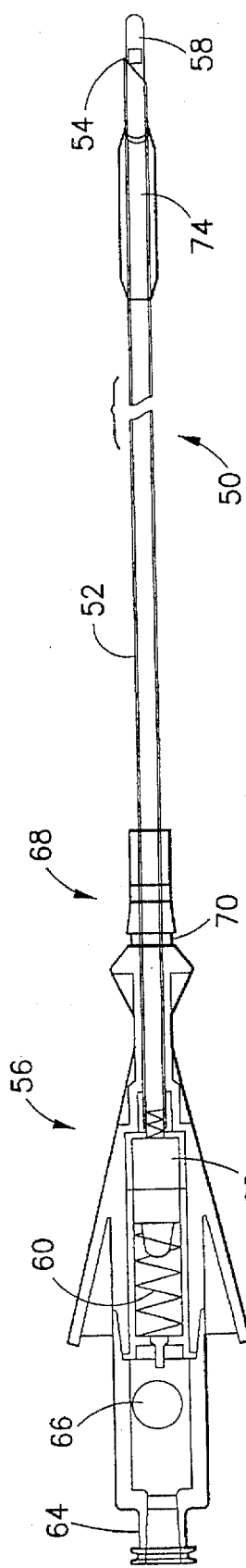
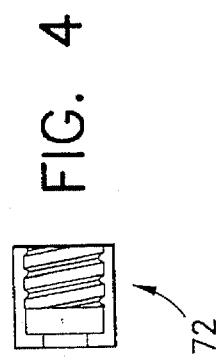
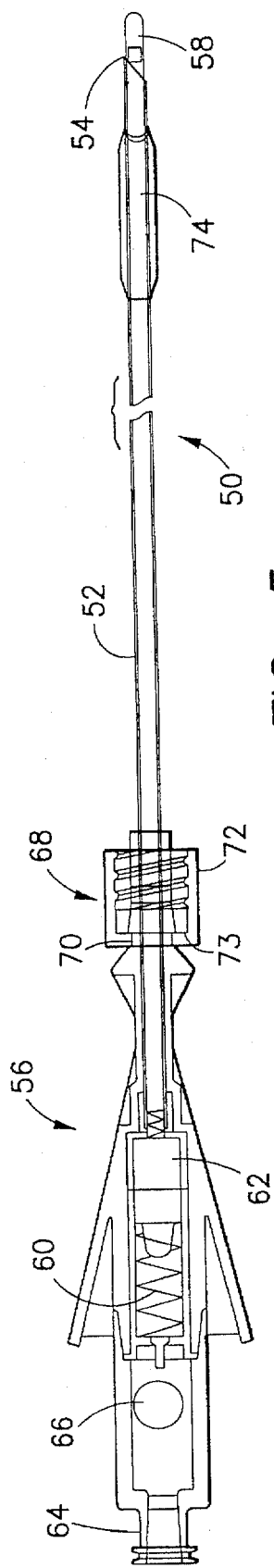
FIG. 3
FIG. 4
FIG. 5

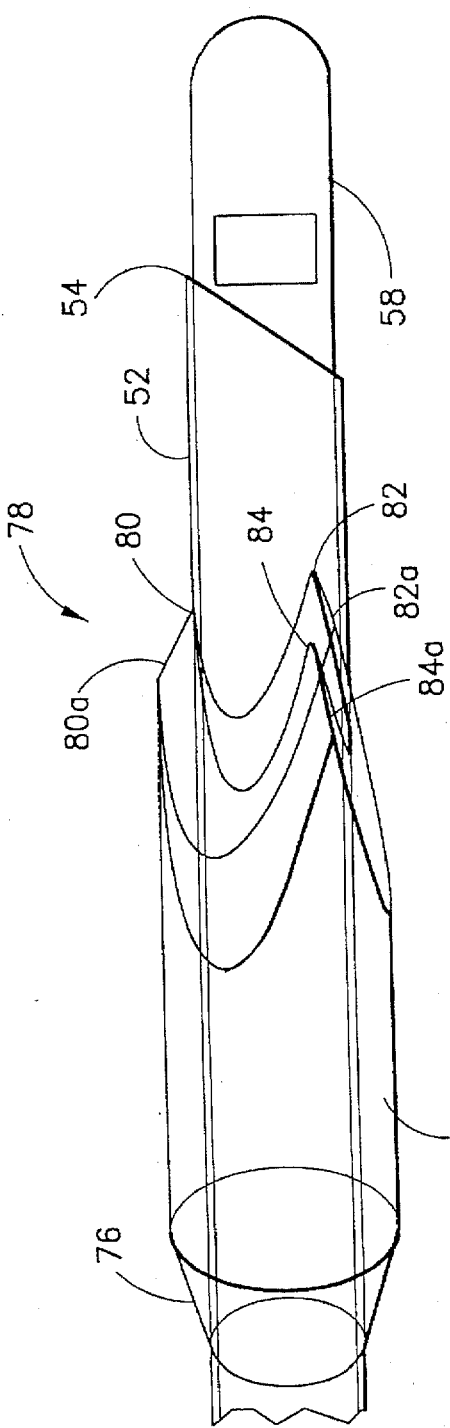
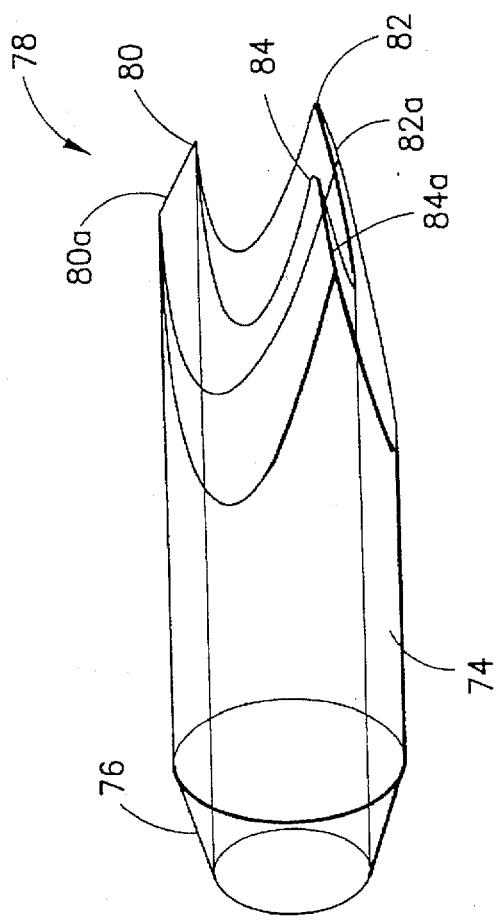
FIG. 6
FIG. 7

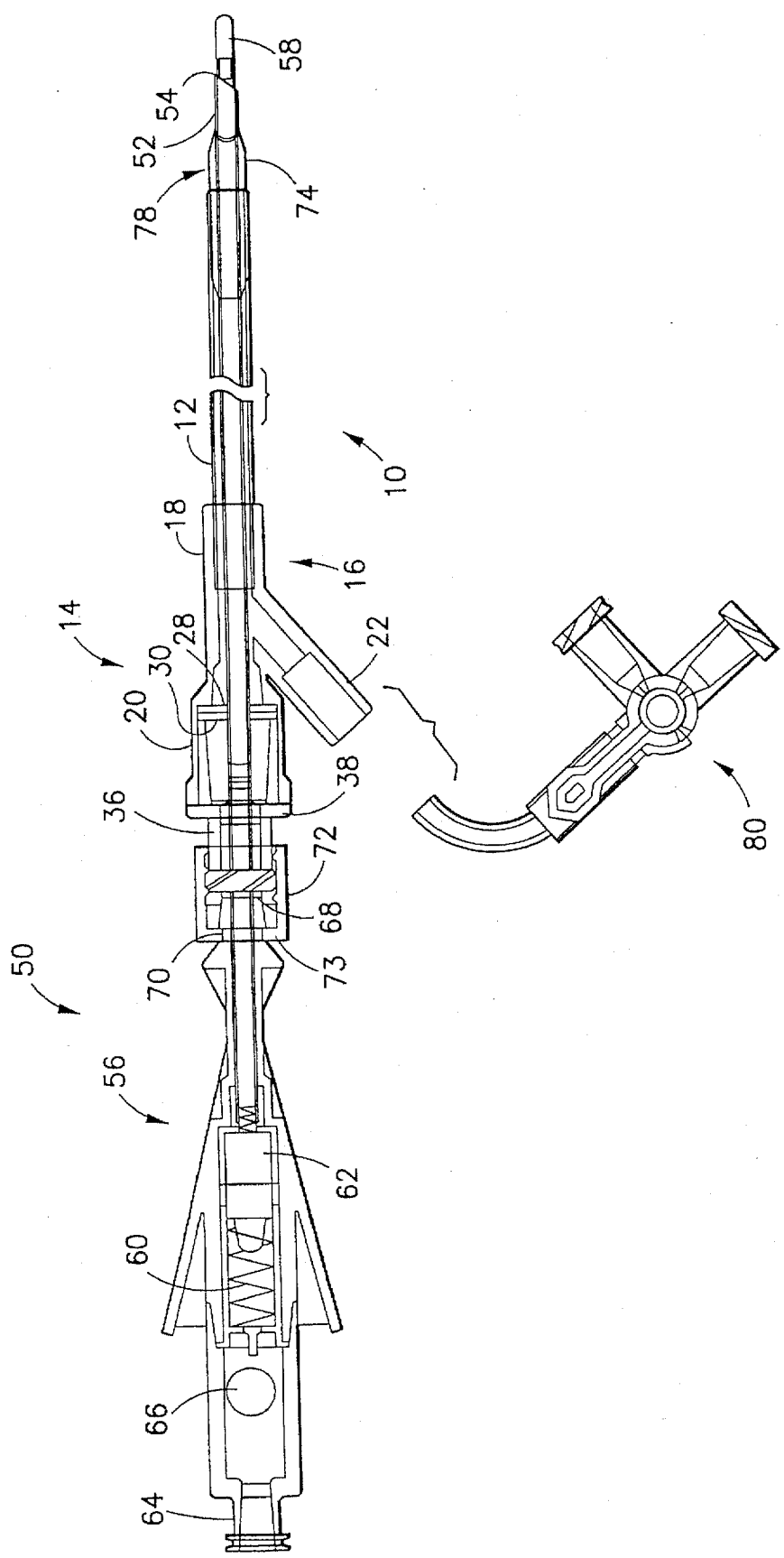

VERESS NEEDLE AND CANNULA ASSEMBLY

This application is related to co-assigned U.S. Pat. No. 5,139,485, the complete disclosure of which is incorporated herein by reference.

BACKGROUND OF THE INVENTION

1. Field of the Invention

The invention relates to surgical instruments. More particularly, the invention relates to a Veress needle and cannula assembly which is insertable into the body for aspiration and insufflation. The Veress needle is removable from the cannula which may then serve as an instrument port.

2. State of the Art

Endoscopic surgery is widely practiced throughout the world today and its acceptance is growing rapidly. In general, endoscopic surgery involves one or more incisions made by trocars (cannulae carrying sharp obturators) where the cannulae are left in place to provide instrument ports so that endoscopic surgical instruments may be inserted into the body. An endoscope is often inserted through one cannula, while a cutter, dissector, or other surgical instrument is inserted through another cannula for purposes of manipulating and/or cutting an internal organ. Sometimes it is desirable to have several cannulae in place at once in order to receive several surgical instruments. In this manner, organs or tissue may be grasped with one surgical instrument, and simultaneously may be cut with another surgical instrument, all under view of the surgeon via the endoscope. In order to enlarge the closed space surrounding the surgical site, a pneumoneedle (or Veress needle) is inserted into the body cavity and the cavity is insufflated by injecting gas (typically $CO_2$) into the cavity through the Veress needle. At the conclusion of the procedure, the body cavity is desufflated (aspirated) by opening a valve on one or more trocar cannulae.

By 1996, it is expected that more than two million additional endosurgeries will be performed per year that, in 1990, were done via open surgery (MedPRO Month, I:12, p.178). The advantages of endoscopic surgery are clear in that it is less invasive, less traumatic and recovery is typically quicker. As a result, many new instruments and devices for use in endosurgery are introduced every year.

One of the reasons why endoscopic surgery is less traumatic is that the trocars used have relatively small diameters, typically 5–10 mm. Thus, the incisions made in the patient's body are quite small as compared to open surgery and these small incisions heal quickly. Nevertheless, 5 mm trocars are less traumatic than 10 mm trocars and Veress needles (which are typically 3 mm or less in diameter) are the least traumatic. Moreover, the fewer number of incisions made during a procedure, the less traumatic the procedure will be.

SUMMARY OF THE INVENTION

It is therefore an object of the invention to provide a Veress needle and cannula assembly which serves to reduce the number of incisions made during an endoscopic procedure.

It is also an object of the invention to provide a Veress needle and cannula assembly which operates like a trocar in that it provides an instrument port when the Veress needle is removed from the cannula.

It is another object of the invention to provide a cannula for use with a Veress needle that has a side port for insufflation and/or desufflation.

It is also an object of the invention to provide a Veress needle and cannula assembly with a quick-connect coupling.

It is still another object of the invention to provide a Veress needle with a cannula obturator.

In accord with these objects which will be discussed in detail below, the Veress needle and cannula assembly of the present invention includes a stainless steel cannula having an outer diameter of approximately 4 mm and a Veress needle having an outer diameter of approximately 3 mm. The cannula is provided with a proximal valve assembly having a side port. The Veress needle is insertable through the valve assembly of the cannula and fits closely therein, or is alternatively provided with a molded transition collar. If provided, the transition collar seals (obturates) the annular space between the interior of the cannula and the exterior of the Veress needle, and preferably provides cutting edges for easing insertion of the assembly into the patient. Both the Veress needle and cannula are provided with locking means such that when the Veress needle is inserted through the cannula they may be locked together.

The cannula valve assembly according to the invention preferably includes a polycarbonate housing, a slit valve or gasket, a wiper gasket, and a polypropylene male luer lock connector. The proximal end of the housing has an increased diameter cylindrical portion which is provided with a pair of protrusion receiving recesses on its interior surface. The slit and wiper gaskets are dimensioned to fit inside against the distal end of the increased diameter cylindrical portion. The polypropylene luer lock connector has a distal cylindrical portion which is dimensioned to fit inside the increased diameter cylindrical portion of the polycarbonate housing and is provided with a pair of ramped radial protrusions which engage and interlock with the protrusion receiving recesses during assembly.

The Veress needle according to the invention preferably includes a hollow outer needle with a sharp distal end, a handle coupled to the proximal end of the outer needle, and a spring biased blunt tipped inner stylet which extends through the outer hollow needle. The inner blunt tipped stylet is normally biased to a position which extends beyond the sharp distal end of the hollow outer needle and is movable against its biasing spring into the hollow outer needle. An indicator in the handle indicates the position of the inner stylet relative to the outer needle. A distal portion of the handle is tapered and has a groove or waist which is arranged to receive and retain a luer lock coupler. A rotatable luer lock coupler is snap-fit onto the waist of the handle. A distal portion of the outer needle may be insert molded with a transition collar which is preferably cylindrical and has tapered proximal and distal ends. The transition collar, if provided, is located on the outer needle such that it extends beyond the distal end of the cannula, and the transition collar is advantageously provided with distal cutting edges which minimize the force required to insert the Veress needle and cannula assembly into the body of the patient.

Additional objects and advantages of the invention will become apparent to those skilled in the art upon reference to the detailed description taken in conjunction with the provided figures.

BRIEF DESCRIPTION OF THE DRAWINGS

FIG. 1 is an exploded transparent side elevation view of the cannula assembly according to the invention;

FIG. 2 is an assembled transparent side elevation view of the cannula assembly according to the invention;

FIG. 3 is a transparent side elevation view of a Veress needle according to the invention;

FIG. 4 is a transparent side elevation view of snap-on luer lock coupler for the Veress needle of FIG. 3;

FIG. 5 is a view similar to FIG. 3 showing the Veress needle with the luer lock coupler of FIG. 4 attached to it;

FIG. 6 is an enlarged broken transparent view of the distal end of the Veress needle and showing a transition collar;

FIG. 7 is an enlarged transparent view of the transition collar of FIG. 6; and

FIG. 8 is a broken side elevational view, partially transparent and partially in section of the Veress needle and cannula assembly of the invention.

DETAILED DESCRIPTION OF THE PREFERRED EMBODIMENTS

Referring now to FIGS. 1 and 2, a cannula assembly 10 includes a substantially cylindrical stainless steel cannula 12 having an outer diameter of approximately 4 mm and a proximal valve assembly 14. The valve assembly 14 preferably includes a polycarbonate housing 16 having a distal cylindrical portion 18 which is dimensioned to fit snugly over the proximal end of the cannula 12, a proximal cylindrical portion 20 having a larger diameter to accommodate valve members as described below, a side port 22 located intermediate of the proximal portion 20 and the distal portion 18, and a proximal polypropylene luer lock connector 23 which engages the proximal cylindrical portion 20. The proximal portion 20 has a pair of diametrically opposed protrusion receiving recesses 24, 26 on its interior surface and is dimensioned to receive a slit gasket (e.g., tricuspid gasket) 28, a wiper gasket (e.g., an O-ring) 30, and the polypropylene male luer lock connector 23. The slit gasket 28 and the wiper gasket 30 are dimensioned to fit inside against the distal end of the proximal cylindrical portion 20 of the polycarbonate housing 16. The polypropylene luer lock connector 23 has a distal cylindrical portion 34, a proximal female luer lock 36, and an annular flange 38 therebetween. The distal cylindrical portion 34 is dimensioned to fit inside the proximal cylindrical portion 20 of the polycarbonate housing 16 and is provided with a pair of diametrically opposed ramped radial protrusions 40, 42 which engage and interlock with the protrusion receiving recesses 24, 26.

The cannula 12 is preferably insert molded in the polycarbonate housing 16. The slit gasket 28 and the wiper gasket 30 are placed inside the proximal portion 20 of the housing 16, and the distal cylindrical portion 34 of the luer lock connector 23 is snapped into the proximal portion 20 of the housing 16 until its radial protrusions 40, 42 engage the recesses 24, 26. In this position, the slit gasket 28 and the wiper gasket 30 are held securely in place at the distal end of the proximal portion 20 and the flange 38 on the luer lock connector 23 seats against the proximal end of the proximal portion 20.

Turning now to FIGS. 3–5, a Veress needle 50 preferably includes a hollow outer needle 52 with a sharp distal end 54, a handle 56 coupled to the proximal end of the outer needle 52, and a spring biased blunt tipped hollow inner stylet 58 which extends through the outer hollow needle 52. The inner blunt tipped stylet 58 is normally biased by a spring 60 in the handle 56 to a position which extends beyond the sharp distal end 54 of the outer needle 52 and is movable against the spring 60 into the hollow needle. An indicator 62 in the handle indicates the position of the inner stylet 58 relative to the sharp distal end 54 of the outer needle 52. A luer connector 64 and a float valve 66 are also provided in the handle 56 and provide fluid communication with the interior of the hollow inner stylet 58. Details regarding the spring 60, indicator 62, luer connector 64, and float valve 66 are disclosed in co-assigned U.S. Pat. No. 5,139,485 which was incorporated herein above. A distal portion 68 of the handle 56 is tapered and has a coupler receiving groove or waist 70. A rotatable luer lock coupler 72 having a proximal collar 73 is snap-fit onto the waist 70 of the handle. If desired, a distal portion of the outer needle 52 may be insert molded into a polycarbonate transition collar 74 which is described in detail below with reference to FIGS. 6 and 7.

Turning now to FIGS. 6 and 7, the transition collar 74 is preferably substantially cylindrical and has tapered proximal and distal ends 76, 78. The distal end 78 of the collar 74 is beveled in three planes thereby providing three sharp points 80, 82, 84 and three cutting edges 80a, 82a, 84a. The purpose of the transition collar 74 is more readily understood with reference to FIG. 8.

Turning now to FIG. 8, the Veress needle 50 according to the invention is seen inserted into the cannula assembly 10 such that the outer needle 52 extends through the cannula 12. The slit gasket 28 and the wiper gasket 30 in the valve assembly 14 seal the spaced surrounding the needle 52 so that fluid access to the space between the needle 52 and the cannula 12 is available only via the side port 22. In this regard, a separate valve assembly 80 may be coupled to the side port 22 as understood by those skilled in the art. The rotatable luer lock coupler 72 on the Veress needle 50 engages and couples with the female luer lock 36 on the cannula assembly 10 thereby locking the Veress needle in the cannula assembly against longitudinal movement. If the Veress needle does not fit closely inside the cannula 12, in order to stabilize the distal end of the Veress needle 50, the transition collar 74 can be used to fill the annular space between the distal portion of the cannula 12 and the Outer needle 52. The transition collar 74 is preferably arranged to minimize the force required to insert the Veress needle and cannula assembly into the body of the patient as the transition collar 74 is located on the outer needle such that it extends beyond the distal end of the cannula and provides cutting edges 80a, 82a, 84a which aid in the insertion procedure.

In use, the Veress needle and cannula assembly is inserted into the patient's body and the surgical site is insufflated via the Veress needle by attaching a source of gas to the luer connector 64. During insertion, the sharp distal end 54 of the outer needle 52 punctures the skin of the patient (the blunt stylet being forced backward) and the sharp edges of the transition collar 74 (where provided) widen the puncture to accommodate the cannula 12. After insertion and insufflation, the rotatable luer lock coupler 72 is rotated and uncoupled from the luer 36 on the cannula assembly and the Veress needle is removed from the cannula assembly. The slit gasket 28 and the wiper gasket 30 seal the proximal end of the cannula assembly so that insufflation gas does not escape from the surgical site. A supplementary source of insufflation gas may be coupled to the side port 22 of the cannula assembly via the valve 80. The cannula assembly remains in place as an access conduit to the surgical site and instruments may be inserted through the cannula assembly with the slit gasket 28 and the wiper gasket 30 sealing the space between the instrument and the cannula so that insufflation gas is maintained at the surgical site.

There have been described and illustrated herein several embodiments of a Veress Needle and a cannula assembly for use therewith. While particular embodiments of the invention have been described, it is not intended that the invention be limited thereto, as it is intended that the invention be as broad in scope as the art will allow and that the specification be read likewise. Thus, while particular materials have been disclosed, it will be appreciated that other materials could be utilized. Also, while a slit gasket and a wiper gasket have been shown in the valve assembly of the cannula assembly, it will be recognized that other types of valve members could be used with similar results obtained. Moreover, while particular configurations have been disclosed in reference to spring and indicator in the handle of the Veress needle, it will be appreciated that other configurations could be used as well. Furthermore, while the sharpened end of the transition collar has been disclosed as having three bevels, it will be understood that different numbers of bevels can achieve the same or similar function as disclosed herein. It will therefore be appreciated by those skilled in the art that yet other modifications could be made to the provided invention without deviating from it's spirit and scope as so claimed.

We claim:

1. A medical apparatus, comprising:
    a) a cannula assembly having
        i) a hollow cannula with a proximal end, a distal end, and an interior diameter,
        ii) a valve assembly coupled to said proximal end of said cannula; and
    b) a Veress needle assembly fitting closely within said hollow cannula and having
        i) an outer hollow needle having a proximal end, a sharp distal end, and an exterior diameter which is smaller than said interior diameter of said hollow cannula, wherein said valve assembly permits insertion of said outer hollow needle into said cannula and fluidly seals the proximal end of said cannula,
        ii) an inner stylet having a proximal end and a blunt distal end, said inner stylet extending through said outer hollow Veress needle;
        iii) a handle coupled to said proximal end of said outer hollow needle, said handle having biasing means for biasing said stylet to a position where said blunt distal end of said stylet extends beyond said sharp distal end of said outer hollow needle; and
        iv) a transition collar mounted on a portion of said outer hollow needle, said transition collar having an inner diameter substantially equal to said exterior diameter of said outer hollow needle and an outer diameter substantially equal to said interior diameter of said hollow cannula to cause said Veress needle assembly to fit closely within said cannula.

2. A medical apparatus according to claim 1, wherein:
    said cannula assembly further includes first coupling means on one of said hollow cannula and said valve assembly, and
    said Veress needle assembly further includes second coupling means for mechanically coupling to said first coupling means.

3. A medical apparatus according to claim 1, wherein:
    said valve assembly includes a slit valve and a wiper gasket.

4. A medical apparatus according to claim 2, wherein:
    said first coupling means comprises a female luer lock and said second coupling means comprises a male luer lock.

5. A medical apparatus according to claim 4, wherein:
    said male luer lock is rotatably coupled to said handle.

6. An assembly according to claim 1, wherein:
    said transition collar has a sharp distal edge which extends beyond said distal end of said hollow cannula when said outer hollow needle is in said cannula.

7. An assembly according to claim 6, wherein:
    said transition collar has a distal end which is bevelled in three planes.

8. A Veress needle assembly for use with a cannula assembly where the cannula assembly includes a hollow cannula with a proximal and a distal end and having an interior diameter, and a valve assembly coupled to the proximal end of the cannula, the Veress needle assembly comprising:
    a) an outer hollow needle having a proximal end, a sharp distal end, and an exterior diameter which is smaller than the interior diameter of the hollow cannula;
    b) an inner stylet having a proximal end and a blunt distal end, said stylet extending through said outer hollow needle;
    c) a handle coupled to said proximal end of said outer hollow needle, said handle having biasing means for biasing said stylet to a position where said blunt distal end of said stylet extends beyond said sharp distal end of said outer hollow needle; and
    d) a transition collar mounted on a portion of said outer hollow needle, said transition collar having an inner diameter substantially equal to said exterior diameter of said outer hollow needle and an outer diameter substantially equal to the interior diameter of the hollow cannula to cause said Veress needle to fit closely within the hollow cannula,
    wherein said Veress needle assembly fits closely within the hollow cannula.

9. A Veress needle assembly according to claim 8, wherein the cannula assembly has a first coupling means on one of the cannula and the valve assembly, said veress needle assembly further comprising:
    e) second coupling means on said handle assembly for mechanically coupling to the first coupling means of the cannula assembly.

10. A Veress needle assembly according to claim 9, wherein:
    the first coupling means comprises a female luer lock and said second coupling means comprises a male luer lock.

11. A Veress needle assembly according to claim 10, wherein:
    said male luer lock is rotatably coupled to said handle.

12. A Veress needle assembly according to claim 8, wherein:
    said transition collar has a sharp distal edge which extends beyond the distal end of the hollow cannula when said outer hollow needle is in the cannula.

13. A Veress needle assembly according to claim 12, wherein:
    said transition collar has a distal end which is bevelled in three planes.

* * * * *